(12) United States Patent
Frey et al.

(10) Patent No.: US 7,368,619 B1
(45) Date of Patent: *May 6, 2008

(54) PROCESS FOR THE PRODUCTION OF DIESEL AND AROMATIC COMPOUNDS

(75) Inventors: Stanley J. Frey, Des Plaines, IL (US); Vasant P. Thakkar, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 656 days.

This patent is subject to a terminal disclaimer.

(21) Appl. No.: 10/868,118

(22) Filed: Jun. 15, 2004

(51) Int. Cl.
- *C07C 4/02* (2006.01)
- *C07C 6/00* (2006.01)
- *C10G 47/00* (2006.01)

(52) U.S. Cl. .................... 585/319; 585/475; 208/108
(58) Field of Classification Search ................ 585/319, 585/475; 208/108
See application file for complete search history.

(56) References Cited

U.S. PATENT DOCUMENTS

| | | | |
|---|---|---|---|
| 4,127,471 A | 11/1978 | Suggitt et al. | 208/60 |
| 4,276,437 A | 6/1981 | Chu | 585/467 |

*Primary Examiner*—Thuan Dinh Dang
(74) *Attorney, Agent, or Firm*—David J Piasecki

(57) ABSTRACT

A process for the production of low sulfur diesel and aromatic compounds wherein $C_9+$ hydrocarbons are hydrocracked to produce low sulfur diesel and a naphtha boiling range stream which is transalkylated in an integrated transalkylation zone to produce xylene.

22 Claims, 1 Drawing Sheet

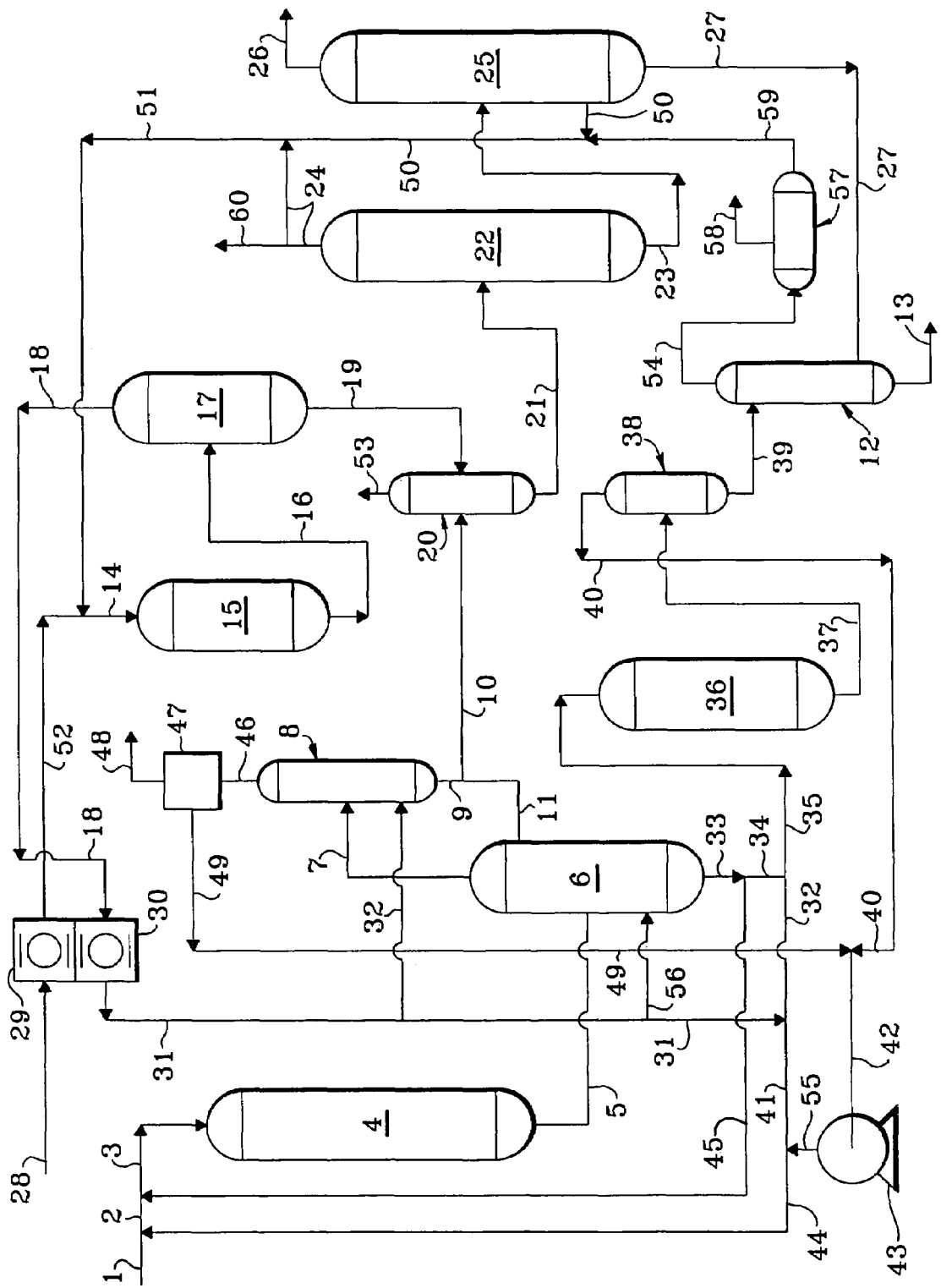

PROCESS FOR THE PRODUCTION OF DIESEL AND AROMATIC COMPOUNDS

BACKGROUND OF THE INVENTION

This invention relates to a process for the conversion of a hydrocarbon feedstock to produce low sulfur diesel and aromatic compounds including xylenes. More specifically, the invention concerns the selective hydrocracking of multi-ring aromatic compounds contained in the hydrocarbon feedstock to produce low sulfur diesel and aromatic compounds which are transalkylated in an integrated transalkylation zone to produce the most desirable xylene isomers.

It has been recognized that due to environmental concerns and newly enacted rules and regulations, saleable products must meet lower and lower limits on contaminants such as sulfur and nitrogen. Recently new regulations require the essentially complete removal of sulfur from liquid hydrocarbons which are used in transportation fuels, such as gasoline and diesel.

The xylene isomers are produced in large volumes from petroleum as feedstocks for a variety of important industrial chemicals. The most important of the xylene isomers is paraxylene, the principal feedstock for polyester which continues to enjoy a high growth rate from a large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand and conversion of other hydrocarbons as necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

Information Disclosure

U.S. Pat. No. 4,276,437 (Chu) teaches the transalkylation and disproportionation of alkylaromatics to yield predominantly the 1,4-alkylaromatic isomer using a zeolite which has been modified by treatment with a compound of a Group IIIB element. The catalyst optionally contains phosphorus, and it is contemplated that the Group IIIB metal is present in the oxidized state.

U.S. Pat. No. 4,127,471 (Suggitt et al.) discloses a process for hydrocracking a charge stock at mild hydrocracking conditions followed by alkyl transfer.

SUMMARY OF THE INVENTION

The present invention is a process for the production of low sulfur diesel and aromatic compounds wherein a hydrocarbonaceous feedstock containing multi-ring aromatic compounds is hydrocracked and partially converted to preferably produce diesel and xylenes. The effluent from the hydrocracker is separated in a hot, high pressure stripper to produce an overhead vapor stream comprising hydrocarbons boiling in the naphtha range and a liquid hydrocarbon stream boiling in the range above naphtha which contains low sulfur diesel and which may be further hydrotreated to saturate aromatic compounds thereby improving the cetane rating. The hydrocarbon boiling in the naphtha range is condensed, stripped of hydrogen sulfide and then introduced into a stripping zone to remove normally gaseous hydrocarbons. At least a portion of the hydrocarbons boiling in the naphtha range is introduced into a transalkylation zone. The sulfide-free hydrogen make-up gas is firstly introduced into the transalkylation zone on a once-thru basis and then further compressed before being introduced into the hydrocracker.

BRIEF DESCRIPTION OF THE DRAWING

The drawing is a simplified process flow diagram of a preferred embodiment of the present invention. The above described drawing is intended to be schematically illustrative of the present invention and is not to be a limitation thereof.

DETAILED DESCRIPTION OF THE INVENTION

The process of the present invention is particularly useful for the production of xylene and diesel from a hydrocarbon feedstock. Suitable hydrocarbon feedstocks boil in the range from about 149° C. (300° F.) to about 399° C. (750° F.) and preferably contain at least about 50 volume percent aromatic compounds. Particularly preferred feedstock contain at least a portion of light cycle oil (LCO) which is a by-product of the fluid catalytic cracking (FCC) process. LCO is an economical and advantageous feedstock since it is undesirable as a finished product and contains significant quantities of sulfur, nitrogen and polynuclear aromatic compounds. Therefore, the present invention is able to convert a low-value LCO stream into valuable xylene hydrocarbon compounds and diesel.

In one preferred embodiment of the present invention the selected feedstock is first introduced into a denitrification and desulfurization reaction zone together with a liquid recycle stream and hydrogen at hydrotreating reaction conditions. Preferred denitrification and desulfurization reaction conditions or hydrotreating reaction conditions include a temperature from about 204° C. (400° F.) to about 482° C. (900° F.), a pressure from about 3.5 MPa (500 psig) to about 17.3 MPa (2500 psig), a liquid hourly space velocity of the fresh hydrocarbonaceous feedstock from about 0.1 $hr^{-1}$ to about 10 $hr^{-1}$ with a hydrotreating catalyst or a combination of hydrotreating catalysts.

The term "hydrotreating" as used herein refers to processes wherein a hydrogen-containing treat gas is used in the presence of suitable catalysts which are primarily active for the removal of heteroatoms, such as sulfur and nitrogen. Suitable hydrotreating catalysts for use in the present invention are any known conventional hydrotreating catalyst and include those which are comprised of at least one Group VII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present invention that more than one type of hydrotreating catalyst be used in the same reaction vessel. The Group VIII metal is typically present in an amount ranging from about 2 to about 20 weight percent, preferably from about 4 to about 12 weight percent. The Group VI metal will typically be present in an amount ranging from about 1 to about 25 weight percent, preferably from about 2 to about 25 weight percent. Typical hydrotreating temperatures range from about 204° C. (400° F.) to about 482° C. (900° F.) with pressures from about 3.5 MPa (500 psig) to about 17.3 MPa (2500 psig), preferably from about 3.5 MPa (500 psig) to about 13.9 MPa (2000 psig).

In accordance with a preferred embodiment of the present invention the resulting effluent from the denitrification and desulfurization zone is introduced into a hydrocracking zone. The hydrocracking zone may contain one or more beds of the same or different catalyst. In one embodiment the preferred hydrocracking catalysts utilize amorphous bases or low-level zeolite bases combined with one or more Group VIII or Group VIB metal hydrogenation components. In another embodiment, the hydrocracking zone contains a catalyst which comprises, in general, any crystalline zeolite cracking base upon which is deposited a minor proportion of a Group VIII metal hydrogenating component. Additional hydrogenation components may be selected from Group VIB for incorporation with the zeolite base. The zeolite cracking bases are sometimes referred to in the art as molecular sieves and are usually composed of silica, alumina and one or more exchangeable cations such as sodium, magnesium, calcium, rare earth metals, etc. They are further characterized by crystal pores of relatively uniform diameter between about 4 and 14 Angstroms. It is preferred to employ zeolites having a silica/alumina mole ratio between about 3 and 12. Suitable zeolites found in nature include, for example, mordenite, stillbite, heulandite, ferrierite, dachiardite, chabazite, erionite and faujasite. Suitable synthetic zeolites include, for example, the B, X, Y and L crystal types, e.g., synthetic faujasite and mordenite. The preferred zeolites are those having crystal pore diameters between about 8-12 Angstroms, wherein the silica/alumina mole ratio is about 4 to 6. A prime example of a zeolite falling in the preferred group is synthetic Y molecular sieve.

The natural occurring zeolites are normally found in a sodium form, an alkaline earth metal form, or mixed forms. The synthetic zeolites are nearly always prepared first in the sodium form. In any case, for use as a cracking base it is preferred that most or all of the original zeolitic monovalent metals be ion-exchanged with a polyvalent metal and/or with an ammonium salt followed by heating to decompose the ammonium ions associated with the zeolite, leaving in their place hydrogen ions and/or exchange sites which have actually been decationized by further removal of water. Hydrogen or "decationized" Y zeolites of this nature are more particularly described in U.S. Pat. No. 3,130,006.

Mixed polyvalent metal-hydrogen zeolites may be prepared by ion-exchanging first with an ammonium salt, then partially back exchanging with a polyvalent metal salt and then calcining. In some cases, as in the case of synthetic mordenite, the hydrogen forms can be prepared by direct acid treatment of the alkali metal zeolites. The preferred cracking bases are those which are at least about 10 percent, and preferably at least 20 percent, metal-cation-deficient, based on the initial ion-exchange capacity. A specifically desirable and stable class of zeolites are those wherein at least about 20 percent of the ion exchange capacity is satisfied by hydrogen ions.

The active metals employed in the preferred hydrocracking catalysts of the present invention as hydrogenation components are those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten. The amount of hydrogenating metal in the catalyst can vary within wide ranges. Broadly speaking, any amount between about 0.05 percent and 30 percent by weight may be used. In the case of the noble metals, it is normally preferred to use about 0.05 to about 2 weight percent. The preferred method for incorporating the hydrogenating metal is to contact the zeolite base material with an aqueous solution of a suitable compound of the desired metal wherein the metal is present in a cationic form. Following addition of the selected hydrogenation metal or metals, the resulting catalyst powder is then filtered, dried, pelleted with added lubricants, binders or the like, if desired, and calcined in air at temperatures of e.g., 371'-648° C. (700'-1200° F.) in order to activate the catalyst and decompose ammonium ions. Alternatively, the zeolite component may first be pelleted, followed by the addition of the hydrogenating component and activation by calcining. The foregoing catalysts may be employed in undiluted form, or the powdered zeolite catalyst may be mixed and copelleted with other relatively less active catalysts, diluents or binders such as alumina, silica gel, silica-alumina cogels, activated clays and the like in proportions ranging between 5 and 90 weight percent. These diluents may be employed as such or they may contain a minor proportion of an added hydrogenating metal such as a Group VIB and/or Group VIII metal.

Additional metal promoted hydrocracking catalysts may also be utilized in the process of the present invention which comprises, for example, aluminophosphate molecular sieves, crystalline chromosilicates and other crystalline silicates. Crystalline chromosilicates are more fully described in U.S. Pat. No. 4,363,718 (Klotz).

The hydrocracking of the hydrocarbonaceous feedstock in contact with a hydrocracking catalyst is conducted in the presence of hydrogen and preferably at hydrocracking reactor conditions which include a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 $hr^{-1}$, and a hydrogen circulation rate from about 337 normal $m^3/m^3$ (2000 standard cubic feet per barrel) to about 4200 $m^3/m^3$ (25000 standard cubic feet per barrel). In accordance with the present invention, the hydrocracking conditions are selected on the basis of the feedstock with the objective of the production of xylene compounds and low sulfur diesel.

The resulting effluent from the hydrocracking zone is introduced into a hot, high pressure stripper to produce a vaporous stream comprising hydrogen, hydrogen sulfide, ammonia and naphtha boiling range hydrocarbons including $C_{10}$-aromatic hydrocarbons, and a first liquid hydrocarbonaceous stream comprising diesel boiling range hydrocarbons. The hot, high pressure stripper is preferably operated at a temperature from about 149° C. (300° F.) to about 288° C. (550° F.) and a pressure from about 3.5 MPa (500 psig) to about 17.3 MPa (2500 psig).

The vaporous stream is partially condensed to produce a liquid hydrocarbon stream comprising hydrocarbons boiling in the range from about 38° C. (100° F.) to about 220° C. (428° F.) including $C_{10}$- aromatic hydrocarbons and a vapor stream comprising hydrogen, hydrogen sulfide and ammonia which vapor stream is treated to remove hydrogen sulfide and ammonia to provide a hydrogen-rich recycle gas. At least a portion of the condensed liquid hydrocarbon stream is stripped to remove normally gaseous hydrocarbon compounds and any dissolved hydrogen sulfide and ammonia. The resulting stripped naphtha boiling range hydrocarbon stream is then fractionated to separate benzene, toluene, xylenes and higher boiling aromatic compounds. In a preferred embodiment, at least a portion of the benzene and toluene, and the 9 and 10 carbon number aromatic compounds are introduced into a transalkylation zone to enhance the production of xylene compounds. A once through hydrogen-rich gaseous stream is also introduced into the transalkylation zone. This gaseous stream is the primary make-up hydrogen to the integrated process and preferably contains at least 98 mol percent hydrogen with essentially no hydrogen sulfide or ammonia. Operating conditions preferably employed in the transalkylation zone normally include a temperature from about 177° C. (350° F.) to about 525° C. (977° F.) and a liquid hourly space velocity in the range from about 0.2 to about 10 $hr^{-1}$.

Any suitable transalkylation catalyst may be utilized in the transalkylation zone. Preferred transalkylation catalysts contain a molecular sieve, a refractory inorganic oxide and a reduced non-framework weak metal. The preferred molecular sieves are zeolitic aluminosilicates which may be any of those which have a silica to alumina ratio greater than about 10 and a pore diameter of about 5 to 8 Angstroms. Specific examples of zeolites which can be used are the MFI, MEL, EUO, FER, MFS, MTT, MTW, TON, MOR, and FAU types of zeolites.

The preparation of the preferred MFI-type zeolites is well known in the art. The zeolites generally are prepared by crystallizing a mixture containing an alumina source, a silica source, an alkali metal source, water and a tetraalkyl ammonium compound or its precursor. The amount of zeolite present in the catalyst can vary considerably but usually is present in an amount from about 30 to 90 mass percent and preferably from about 50 to 70 mass percent of the catalyst.

A refractory binder or matrix preferably is utilized to facilitate fabrication of the transalkylation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, zinc oxide and silica. Alumina and/or silica are preferred binders.

One suitable example of a binder or matrix component is a phosphorus-containing alumina (hereinafter referred to as aluminum phosphate) component. The phosphorus may be incorporated with the alumina in any acceptable manner known in the art. One preferred method of preparing this aluminum phosphate is that described in U.S. Pat. No. 4,629,717 which is incorporated by reference. The technique described in the '717 patent involves the gellation of a hydrosol of alumina which contains a phosphorus compound using the well known oil drop method. Generally this technique involves preparing a hydrosol by digesting aluminum in aqueous hydrochloric acid at reflux temperatures of about 80 to 105° C. The ratio of aluminum to chloride in the sol ranges from about 0.7:1 to 1.5:1 mass ratio. A phosphorus compound is now added to the sol. Preferred phosphorus compounds are phosphoric acid, phosphorous acid and ammonium phosphate. The relative amount of phosphorus and aluminum expressed in molar ratios ranges from about 1:1 to 1:100 on an elemental basis. The resulting aluminum phosphate hydrosol mixture then is gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours. The amount of phosphorus-containing alumina component present (as the oxide) in the catalyst can range from about 10 to 70 mass percent and preferably from about 30 to 50 mass percent.

The zeolite and aluminum phosphate binder are mixed and formed into particles by means well known in the art such as gellation, pilling, nodulizing, marumerizing, spray drying, extrusion any combination of these techniques. A preferred method of preparing the zeolite/aluminum phosphate support involves adding the zeolite either to an alumina sol or a phosphorus compound, forming a mixture of the alumina sol/zeolite/phosphorus compound which is now formed into particles by employing the oil drop method described above. The particles are calcined as described above to provide a support for the metal component.

Another component of a preferred catalyst is a weak non-framework metal. The metal is present in the finished catalyst primarily in a reduced state, i.e., over about 50% of the metal, preferably at least about 75%, and more preferably at least about 90%, of the metal is present in the catalyst in an oxidation state of less than +3. The weak metal promotes $H_2/D_2$ exchange without effecting methylcyclohexane dehydrogenation at a temperature of between about 300° and 500° C. Preferably the metal is selected from the group consisting of platinum, palladium, nickel, tungsten, gallium, rhenium and bismuth, more preferably consists essentially of either gallium or bismuth, and most preferably consists essentially of gallium.

In the preparation of a preferred catalyst, a gallium or bismuth component may be deposited onto the support in any suitable manner to effect the disclosed characteristics of the catalyst. A gallium component suitably is deposited onto the support by impregnating the support with a salt of the gallium metal. The particles are impregnated with a gallium salt selected from the group consisting of gallium nitrate, gallium chloride, gallium bromide, gallium hydroxide, gallium acetate, and the like. Suitable bismuth salts comprise, for example, bismuth nitrate, bismuth acetate, bismuth trichloride, bismuth tribromide, and bismuth trioxide. The amount of gallium and/or bismuth which is deposited onto the support varies from about 0.1 to 5 mass percent of the finished catalyst, expressed as the elemental metal.

The gallium and/or bismuth component may be impregnated onto the support particles by any technique well known in the art such as dipping the catalyst into a solution of the metal compound or spraying the solution onto the support. One preferred method of preparation involves the use of a steam jacketed rotary dryer. The support particles are immersed in the impregnate solution contained in the dryer and the support particles are tumbled therein by the rotating motion of the dryer. Evaporating of the solution in contact with the tumbling support is expedited by applying steam to the dryer jacket. After the particles are completely dry, they are heated under a hydrogen atmosphere at a temperature of about 500° to 700° C. for a time of about 1 to 15 hours. Although a pure hydrogen atmosphere is preferred to reduce and disperse the metal, the hydrogen may be diluted with nitrogen. Next the hydrogen treated particles are heated in air and steam at a temperature of about 400° to 700° C. for a time of about 1 to 10 hours. The amount of steam present in the air varies from about 1 to 40 percent.

The resulting effluent from the transalkylation zone is introduced into a vapor-liquid separator to provide a hydrogen-rich gaseous stream which is compressed and used as make-up hydrogen for the hydrocracking zone. The naphtha boiling range liquid hydrocarbon from the vapor-liquid separator is stripped to remove hydrocarbons boiling at a temperature lower than benzene and then sent to a fractionation section to separate benzene, toluene, xylenes and higher boiling aromatic compounds. In a preferred embodiment, the benzene and toluene would be recycled to the transalkylation zone to maximize the yield of the most valuable xylenes. In the event that more benzene and toluene is desired at the expense of xylene production, they may be directed to product tanks. For example, if the operator wishes to produce additional high octane gasoline, the benzene/toluene net product flow rate would be increased and the overall xylene production would thereby decrease. This readily available feature affords a very flexible way to produce different product slates.

In accordance with the present invention, the hydrogen make-up gas is compressed in a first stage compressor to a pressure suitable for introduction into the transalkylation zone. After flowing through the transalkylation zone, the hydrogen-rich gas is separated and sent to a second stage compressor whereinafter the hydrogen-rich gas is sent to four potential locations, namely, 1) stripping gas service for the hot high pressure stripper, 2) naphtha stripper, 3) make-up gas to an aromatic hydrogenation zones and 4) make-up gas directly to the hydrocracking zone. The cascaded use of hydrogen make-up gas first through the transalkylation zone eliminates the need for a separate recycle gas compressor for the transalkylation zone and the aromatic hydrogenation zone. The hydrogen-rich gas from the top of the naphtha stripper is preferably amine treated to remove hydrogen sulfide and water washed to remove ammonia and sent to the hydrocracking zone recycle gas compressor which then sends the recycle hydrogen gas to two potential locations, namely, the aromatic hydrogenation zone and the hydrocracking zone.

The liquid hydrocarbon stream recovered from the bottom of the hot, high pressure stripper and boiling generally above the boiling range of naphtha and in the boiling range of diesel, may have in one embodiment a portion recycled to the hydrocracking zone and in a second embodiment have at least a portion reacted in an aromatic hydrogenation zone. Any suitable hydrotreating catalyst may be utilized to hydrogenate the aromatic compounds in order to improve the cetane number. In another embodiment, the entire stream may be recovered as a low sulfur diesel product stream.

DETAILED DESCRIPTION OF THE DRAWING

The drawing is a simplified process flow diagram of a preferred embodiment of the present invention. The drawing is intended to be schematically illustrative of the present invention and not to be a limitation thereof.

A liquid hydrocarbonaceous feedstock containing light cycle oil is introduced into the process via line 1 and is admixed with a hereinafter described hydrogen rich gaseous stream provided by line 44. The resulting admixture is transported via line 2 and is joined by a hereinafter described liquid hydrocarbonaceous recycle stream provided by line 45. This resulting admixture is transported via line 3 and introduced into hydrotreating/hydrocracking zone 4. The resulting effluent from hydrotreating/hydrocracking zone 4 is transported via line 5 and introduced into hot, high pressure stripper 6. A hot vaporous stream is removed from hot vapor liquid separator 6 via line 7, partially condensed and introduced into naphtha stripper 8. A hydrogen rich gaseous stream is removed from naphtha stripper 8 via line 46 and introduced into amine scrubber 47. Hydrogen sulfide and ammonia are removed from amine scrubber 47 via line 48 and recovered. A hydrogen-rich gaseous stream having a reduced concentration of hydrogen sulfide and ammonia is removed from amine scrubber 47 and is transported via line 49. A liquid hydrocarbonaceous stream containing naphtha is removed from naphtha stripper 8 via line 9 and a portion is introduced into hot vapor liquid stripper 6 via line 11 as reflux and another portion is transported via line 10 and introduced into stripper 20. A hydrogen rich gaseous stream containing essentially no hydrogen sulfide is introduced via line 28 into first stage makeup compressor 29 and the resulting compressed hydrogen rich gas is transported via line 52 and introduced via line 14 into transalkylation zone 15. A resulting effluent from transalkylation zone 15 is transported via line 16 and introduced into vapor liquid separator 17. A hydrogen-rich gaseous stream is removed from vapor liquid separator 17 via line 18 and introduced into second stage makeup compressor 30 to produce a compressed hydrogen-rich gaseous stream carried via line 31. A liquid hydrocarbonaceous stream containing transalkylated hydrocarbons is removed from vapor liquid separator 17 via line 19 and introduced into stripper 20. A vaporous stream containing normally gaseous hydrocarbons is removed from stripper 20 via line 53 and recovered. A liquid hydrocarbonaceous stream is removed from stripper 20 via line 21 and introduced into fractionation zone 22. A stream containing benzene and toluene is removed from fractionation zone 22 via line 24 and a portion is transported via lines 51 and 14 and introduced into transalkylation zone 15. Another portion of the stream containing benzene and toluene is removed from fractionation zone 22 via lines 24 and 60, and recovered. A liquid stream containing $C_8+$ aromatic compounds is removed from fractionation zone 22 via line 23 and introduced into fractionation zone 25. A stream containing xylenes is removed from fractionation zone 25 via line 26 and recovered. A sidecut stream containing $C_9$ and $C_{10}$ aromatic compounds is removed from fractionation zone 25 via line 50 and introduced via lines 50, 51 and 14 into transalkylation zone 15. A hydrocarbon stream containing $C_{10}+$ aromatic compounds is removed from fractionation zone 25 via line 27 and introduced into fractionation zone 12 to produce an ultra low sulfur diesel stream transported via line 13 and removed from fractionation zone 12. A liquid hydrocarbon stream containing hydrocarbons boiling above the naphtha range is removed from hot, high pressure stripper 6 via line 33 and a portion is transported via lines 45 and 3 and introduced into hydrotreating/hydrocracking zone 4 as the hereinabove described liquid hydrocarbon recycle stream and another portion is transported via lines 34 and 35 and introduced into aromatics hydrogenation zone 36. A resulting effluent from aromatics hydrogenation zone 36 is transported via line 37, partially condensed and introduced into vapor liquid separator 38. A liquid hydrocarbon stream containing hydrocarbons boiling in the range greater than naphtha and having a low concentration of sulfur is removed from vapor liquid separator 38 via line 39 and introduced into fractionation zone 12. A hydrogen-rich gaseous stream is removed from vapor liquid separator 38 via line 40 and is joined by a hydrogen-rich gaseous stream which is provided via line 49 as previously described and the resulting admixture is transported via line 42 and introduced into recycle compressor 43. A resulting compressed hydrogen-rich gaseous stream is removed from recycle compressor 43 via line 55 and a portion is carried via lines 44, 2 and 3 and introduced into hydrotreating/hydrocracking zone 4 as hydrogen-rich recycle gas as hereinabove described and another portion is carried via line 41 and is joined by a hydrogen-rich gaseous stream provided via line 31 as described hereinabove and the resulting admixture is transported via lines 32 and 35 and introduced into aromatics hydrogenation zone 36. A hydrogen-rich gaseous stream is provided via lines 31 and 32 and introduced into naphtha stripper 8. Another hydrogen-rich gaseous stream is provided via lines 31 and 56 and introduced into hot, high pressure stripper 6.

The foregoing description and drawing clearly illustrate the advantages encompassed by the process of the present invention and the benefits to be afforded with the use thereof.

What is claimed is:

1. A process for the production of low sulfur diesel and aromatic compounds which process comprises:
   (a) reacting a hydrocarbonaceous stream comprising $C_9+$ hydrocarbons in a hydrocracking zone containing a hydrocracking catalyst to produce a hydrocracking zone effluent comprising xylenes;
   (b) passing the hydrocracking zone effluent into a hot high pressure stripper to produce an overhead vapor stream comprising hydrocarbons boiling in the range from about 38° C. (100° F.) to about 220° C. (428° F.) and a liquid hydrocarbon stream comprising hydrocarbons boiling above about 220° C. (428° F.);
   (c) condensing at least a portion of the overhead vapor stream comprising hydrocarbons boiling in the range from about 38° C. (100° F.) to about 220° C. (428° F.) to produce a liquid hydrocarbon stream comprising hydrocarbons boiling in the range from about 38° C. (100° F.) to about 220° C. (428° F.);
   (d) separating and reacting at least a portion of the liquid hydrocarbon stream produced in step (c) and make-up hydrogen in a transalkylation zone to produce a liquid hydrocarbonaceous transalkylation effluent and a gaseous stream comprising hydrogen;
   (e) passing at least a portion of the gaseous stream comprising hydrogen produced in step (d) to the hydrocracking zone, and
   (f) recovering xylenes.

2. The process of claim 1 wherein the hydrocarbonaceous stream comprising $C_9+$ hydrocarbons comprises light cycle oil.

3. The process of claim 1 wherein the hot high pressure stripper is operated at a temperature from about 149° C. (300° F.) to about 288° C. (550° F.) and a pressure from about 3.5 MPa (500 psig) to about 17.3 MPa (2500 psig).

4. The process of claim 1 wherein the hydrocracking zone is operated at conditions including a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 $hr^{-1}$ and a hydrogen circulation rate from about 337 $nm^3/m^3$ (2000 standard cubic feet per barrel) to about 4200 $nm^3/m^3$ (25,000 standard cubic feet per barrel).

5. The process of claim 1 wherein the transalkylation zone is operated at conditions including a temperature from about 177° C. (350° F.) to about 525° C. (977° F.) and a liquid hourly space velocity in the range from about 0.2 to about 10 $hr^{-1}$.

6. The process of claim 1 wherein the hydrocracking zone contains hydrocracking catalyst and hydrotreating catalyst.

7. The process of claim 1 wherein at least a portion of the liquid hydrocarbon stream comprising hydrocarbons boiling above about 220° C. (428° F.) produced in step (b) is recycled to the hydrocracking zone.

8. The process of claim 1 wherein at least a portion of the liquid hydrocarbon stream comprising hydrocarbons boiling above about 220° C. (428° F.) produced in step (b) is reacted in an aromatics hydrogenation reaction zone.

9. A process for the production of low sulfur diesel and aromatic compounds which process comprises:
   (a) reacting a hydrocarbonaceous stream comprising $C_9+$ hydrocarbons in a hydrocracking zone containing a hydrocracking catalyst to produce a hydrocracking zone effluent comprising xylenes;
   (b) passing the hydrocracking zone effluent into a hot high pressure stripper to produce an overhead vapor stream comprising hydrocarbons boiling in the range from about 38° C. (100° F.) to about 220° C. (428° F.) and a liquid hydrocarbon stream comprising hydrocarbons boiling above about 220° C. (428° F.);
   (c) condensing at least a portion of the overhead vapor stream comprising hydrocarbons boiling in the range from about 38° C. (100° F.) to about 220° C. (428° F.) to produce a liquid hydrocarbon stream comprising hydrocarbons boiling in the range from about 38° C. (100° F.) to about 220° C. (428° F.);
   (d) separating and reacting at least a portion of the liquid hydrocarbon stream produced in step (c) and make-up hydrogen in a transalkylation zone to produce a liquid hydrocarbonaceous transalkylation effluent and a gaseous stream comprising hydrogen;
   (e) passing at least a portion of the gaseous stream comprising hydrogen produced in step (d) to the hydrocracking zone;
   (f) passing at least a portion of the liquid hydrocarbon stream comprising hydrocarbons boiling above about 220° C. (428° F.) produced in step (b) to the hydrocracking zone; and
   (g) recovering xylenes.

10. The process of claim 9 wherein the hydrocarbonaceous stream comprising $C_9+$ hydrocarbons comprises light cycle oil.

11. The process of claim 9 wherein the hot high pressure stripper is operated at a temperature from about 149° C. (300° F.) to about 288° C. (550° F.) and a pressure from about 3.5 MPa (500 psig) to about 17.3 MPa (2500 psig).

12. The process of claim 9 wherein the hydrocracking zone is operated at conditions including a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 $hr^{-1}$ and a hydrogen circulation rate from about 338 $nm^3/m^3$ (2000 standard cubic feet per barrel) to about 4200 $nm^3/m^3$ (25,000 standard cubic feet per barrel).

13. The process of claim 9 wherein the transalkylation zone is operated at conditions including a temperature from about 177° C. (350° F.) to about 525° C. (977° F.) and a liquid hourly space velocity in the range from about 0.2 to about 10 $hr^{-1}$.

14. The process of claim 9 wherein the hydrocracking zone contains hydrocracking catalyst and hydrotreating catalyst.

15. The process of claim 9 wherein at least a portion of the liquid hydrocarbon stream comprising hydrocarbons boiling above about 220° C. (428° F.) produced in step (b) is reacted in an aromatics hydrogenation reaction zone.

16. A process for the production of low sulfur diesel and aromatic compounds which process comprises:

(a) reacting a hydrocarbonaceous stream comprising $C_9$+ hydrocarbons in a hydrocracking zone containing a hydrocracking catalyst to produce a hydrocracking zone effluent comprising xylenes;

(b) passing the hydrocracking zone effluent into a hot high pressure stripper to produce an overhead vapor stream comprising hydrocarbons boiling in the range from about 38° C. (100° F.) to about 220° C. (428° F.) and a liquid hydrocarbon stream comprising hydrocarbons boiling above about 220° C. (428° F.);

(c) condensing at least a portion of the overhead vapor stream comprising hydrocarbons boiling in the range from about 38° C. (100° F.) to about 220° C. (428° F.) to produce a liquid hydrocarbon stream comprising hydrocarbons boiling in the range from about 38° C. (100° F.) to about 220° C. (428° F.);

(d) separating and reacting at least a portion of the liquid hydrocarbon stream produced in step (c) and makeup hydrogen in a transalkylation zone to produce a liquid hydrocarbonaceous transalkylation effluent and a gaseous stream comprising hydrogen;

(e) passing at least a portion of the gaseous stream comprising hydrogen produced in step (d) to the hydrocracking zone;

(f) reacting at least a portion of the liquid hydrocarbon stream comprising hydrocarbons boiling above 220° C. (428° F.) produced in step (b) in an aromatic hydrogenation reaction zone; and (g) recovering xylenes.

17. The process of claim 16 wherein the hydrocarbonaceous stream comprising $C_9$+ hydrocarbons comprises light cycle oil.

18. The process of claim 16 wherein the hot high pressure stripper is operated at a temperature from about 149° C. (300° F.) to about 288° C. (550° F.) and a pressure from about 3.5 MPa (500 psig) to about 17.3 MPa (2500 psig).

19. The process of claim 16 wherein the hydrocracking zone is operated at conditions including a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 $hr^{-1}$ and a hydrogen circulation rate from about 338 $nm^3/m^3$ (2000 standard cubic feet per barrel) to about 4200 $nm^3/m^3$ (25,000 standard cubic feet per barrel).

20. The process of claim 16 wherein the transalkylation zone is operated at conditions including a temperature from about 177° C. (350° F.) to about 525° C. (977° F.) and a liquid hourly space velocity in the range from about 0.2 to about 10 $hr^{-1}$.

21. The process of claim 16 wherein the hydrocracking zone contains hydrocracking catalyst and hydrotreating catalyst.

22. The process of claim 16 wherein at least a portion of the liquid hydrocarbon stream comprising hydrocarbons boiling above about 220° C. (428° F.) produced in step (b) is recycled to the hydrocracking zone.

* * * * *